United States Patent [19]

Vollhardt

[11] Patent Number: 4,632,587
[45] Date of Patent: Dec. 30, 1986

[54] REACTOR CONSTRUCTION

[75] Inventor: Frohmut Vollhardt, Oberhausen, Fed. Rep. of Germany

[73] Assignee: M.A.N. Maschinenfabrik Augsburg-Nurnberg Aktiengesellschaft, Oberhausen, Fed. Rep. of Germany

[21] Appl. No.: 637,759

[22] Filed: Aug. 6, 1984

[30] Foreign Application Priority Data

Sep. 6, 1983 [DE] Fed. Rep. of Germany ....... 3332049
Dec. 8, 1983 [DE] Fed. Rep. of Germany ....... 3344423

[51] Int. Cl.$^4$ ............................................. F28D 21/00
[52] U.S. Cl. .................................... 422/202; 422/196; 422/201; 422/239; 422/312
[58] Field of Search ............... 422/202, 239, 312, 201, 422/200, 196

[56] References Cited

U.S. PATENT DOCUMENTS

| | | | |
|---|---|---|---|
| 1,920,800 | 8/1933 | McCausland | 422/201 X |
| 2,149,300 | 3/1939 | Lassiat | 422/201 |
| 2,261,293 | 11/1941 | Samans | 422/200 |
| 2,280,081 | 4/1942 | Prickett et al. | 422/201 |
| 2,356,700 | 8/1944 | Rupp et al. | 422/202 |
| 2,862,480 | 12/1958 | Oberg | 422/201 X |

*Primary Examiner*—Arthur Kellogg
*Attorney, Agent, or Firm*—McGlew and Tuttle

[57] ABSTRACT

A reactor comprises a vertically elongated cylindrical housing with at least one bottom in the housing which supports a catalyst bed which is permeable to gas and through which heat exchanger tubes extend. The construction includes a cylindrical wall within the housing which encloses the catalyst. The housing is constructed so that a cover thereof may be removed to lift the bottom together with the cylindrical wall and the catalyst bed with the tubes out of the housing. The cylindrical wall is advantageously formed by finned tubes. The construction advantageously includes upper and lower header portions and the heat exchanger tubes which extend through the bed are bent at each end and extend into these headers. In an alternate embodiment, the reactor has more than one bottom at spaced vertical locations. Coolant is advantageously supplied through one of the headers of the heat exchanger tubes, for example, a lower one for exit out through the upper one. In addition, gases are circulated for example, through the catalyst bed upwardly. In the case of multiple bottoms, the gas may be admitted intermediate the length of the reactor and circulated both upwardly and downwardly through the catalyts beds.

6 Claims, 5 Drawing Figures

REACTOR CONSTRUCTION

FIELD AND BACKGROUND OF THE INVENTION

This invention relates in general to reactor vessels and in particular to a new and useful reactor for producing a gas such as methanol in which a vertically elongated cylindrical housing contains a catalyst bed which is permeable to gas and which overlies a bottom and is surrounded by a cylindrical wall in a manner such that the catalyst bed may be removed upwardly through the vessel after the cover is removed.

Such reactors are known in a variety of designs. For example, German OS No. 30 07 203 discloses a reactor of this kind having a cylindrical housing, a catalyst filling within the housing, and exchanger tubes extending through the catalyst bed to conduct a coolant, with the tubes extending within the catalyst bed straightly and substantially parallel to the housing axis. To obtain satisfactorily crowded heating surfaces and a low gas pressure drop at the same time, the exchanger tubes are provided with fins or ribs.

SUMMARY OF THE INVENTION

The invention is directed to a methanol reactor permitting both the changing of the catalyst filling and the monitoring or replacement of the heat exchanger tubes in the catalyst bed as well as the renewal of the catalyst bottom or screen in an easy way, while preserving a simple construction of the reactor.

At the same time, the flow conditions in the catalyst bed are to be improved, to extend the life of the exchange tubes, as compared to prior art tubes having the same purpose.

In accordance with the invention, a reactor vessel includes a vertically elongated cylindrical housing having at least one bottom supporting a permeable catalyst bed through which heat exchange tubes extend and which are enclosed by an interior cylindrical wall arranged in the housing beneath a cover which is removable so that the whole bed may be removed.

The invention offers advantages in that the cylindrical wall, preferably made of finned tubes, along with the catalyst bed, can be lifted out of the housing which comprises a pressure jacket and an insulating shell. Then, only the catalyst bottom or screen needs to be loosened partly or completely, to let the catalyst out from the cylindrical enclosure downwardly. Upon closing the bottom or screen again, the cylindrical space, preferably bounded by a wall of finned tubes, may be refilled with the catalyst. The same goes for the replacement of exchange tubes.

It is not necessary to remove the exchange tubes from the housing. They are easily accessible and may individually be dismounted from, or secured again to, the cylindrical wall which is open above over its entire cross section. The flow conditions within the catalyst bed are improved by providing that the tubes form geometrically regular flow passageways therebetween, which are virtually closed in themselves and prevent the gas from straying into adjacent passages, so that the exchange tubes are contacted uniformly. To provide heat exchanger tubes with fins so as to form close passages with regular cross sections, is known in itself from German OS No. 15 01 640, where this idea is applied particularly to the cooling of fresh cracked gases and/or synthesis gas. The inventive reactor differs therefrom by making use of the passages between the tubes for filling them with the catalyst.

The advantage of finned exchange tubes provided with pins projecting into the flow passages is that beneath the pins, the catalyst mass is relieved of its overburden, so that at those locations, it becomes loosened in its structure and the flow conditions within the catalyst bed are improved. The pins further intensify the heat transfer from the catalyst to the tubes and thus to the exchange fluid.

In itself, it is known in various technologies to provide pins on walls, such as walls of smelting chambers, to help to support the plastic refractory or other lining of the smelting chamber. In the present invention, however, the purpose and effect are different.

The inventive reactor is suitable not only for producing methanol, it may also serve to conduct other catalytic reactions.

Accordingly it is an object of the invention to provide an improved reactor vessel in which the catalyst bed is supported on at least one bottom within a cylindrical housing which has a cover which may be removed such that an interior cylindrical wall which encloses the catalyst bed and the bottom with the exchanger tubes running through the bed may be lifted out of the vessel.

A further object of the invention is to provide a reactor for producing a gas such as methanol which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE PREFERRED EMBODIMENTS

DESCRIPTION OF THE PREFERRED EMBODIMENTS

Figures 1, 2:
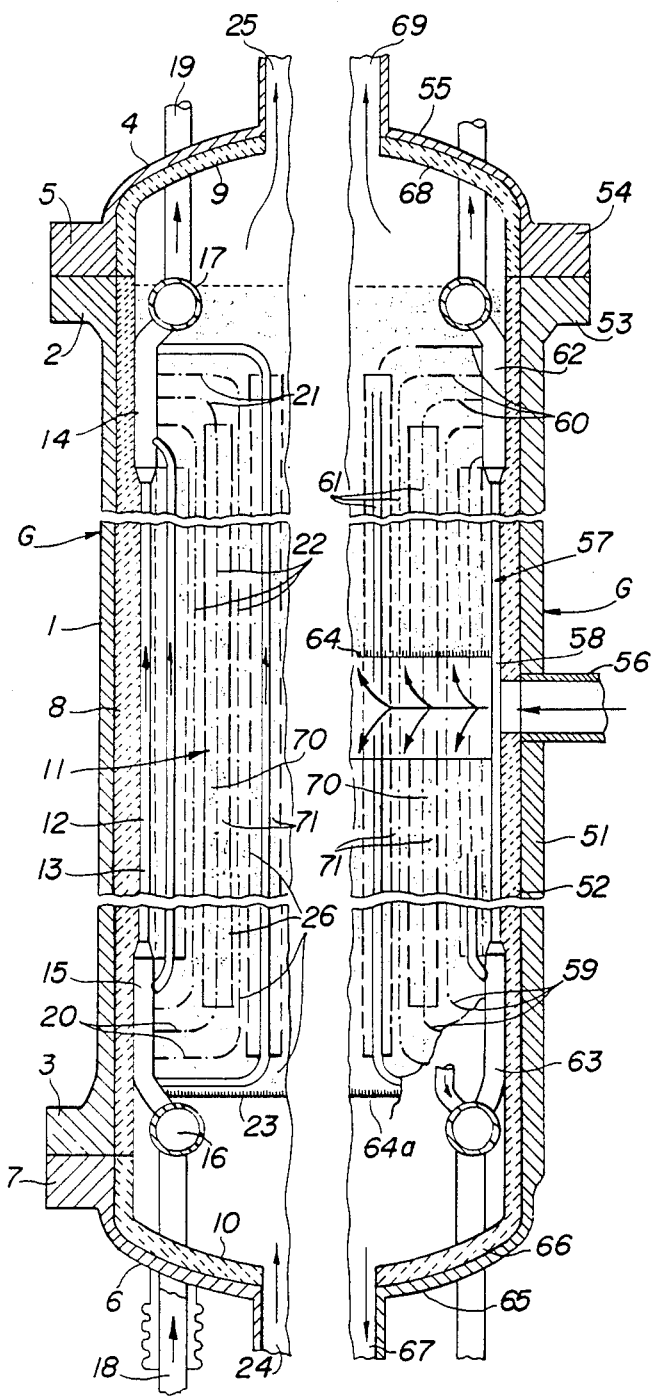
FIG. 1 is an axial sectional view of a first embodiment of the invention comprising a reactor with a catalyst bed, in a sectional view.
FIG. 2 is a sectional view of another embodiment in which two catalyst beds are provided.
Figure 3:
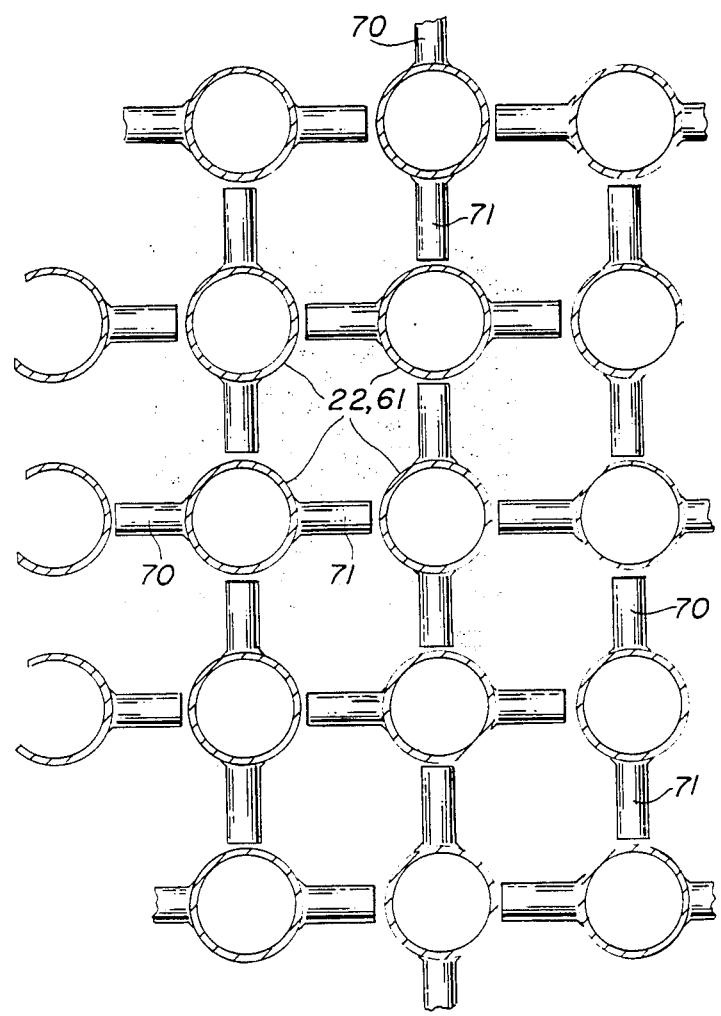

Referring to the drawings in particular the invention embodied therein in FIG. 1 comprises a reactor including a vertically elongated cylindrical housing 1 having at least one bottom 23 which supports a catalyst mass 26 which is permeable to gas which has heat exchanger tubes 22 extending therethrough. In accordance with the invention a cylindrical outer wall advantageously is made of finned tubes generally designated 13 closes the reactor bed and the tubes so that the bottom including the wall may lifted upwardly out of the housing 1 when a cover 4 is removed therefrom. Alternatively, the assembly may be removed to the other end, for example when a cover or bottom 6 is removed from the housing.

Referring to the embodiment shown in FIG. 1, the reactor comprises a housing G formed by an outer cylindrical pressure jacket 1 extending from the upper to the lower section of the reactor and having a flange 2,3 on respective upper and lower rims. On its top, housing 6 is covered by a cover 6 having a flange 5 by means of which the cover is connected to flange 2 of the cylindrical pressure jacket. The bottom 6 of housing G is connected through its flange 7 to flange 3 of the housing.

Pressure jacket 1 is lined with an insulating layer 8 extending from the joint between flanges 2 and 5 to the joint between flanges 3 and 7. Cover 4 and bottom 6 also are lined with insulating layer portions 9,10. Pressure jacket 1, cover 4, and bottom 6 with their linings are designed to allow the removal of the cover 4 from jacket 1 without difficulties. The same goes for the bottom 6, if necessary.

An insulating layer 8 forms a lining of the cylindrical jacket 1 and it encloses the central portion of a heat exchanger 11. The heat exchanger 11 comprises a cylindrical outer wall 13 of finned tubes 12. The upper and lower ends of finned tubes 12 open into wider tube portions 14,15 which in turn open into a lower distributor ring 16 and an upper collector ring 17. In the embodiment pf FIG. 1, coolant is supplied into exchanger 11 through one or more pipes 18 extending through bottom 6 and insulating layer 10, and leaves collector ring 17 through one or more pipes 19.

Heat exchanger 11 further comprises a nest of vertically extending exchange tubes 22 having horizontally bent end portions 20 by which they open into the wider tube portions 14,15 of the cylindrical outer wall 13 of the exchanger.

At the level of distributor ring 16, as shown in FIG. 1, slightly thereabove, a catalyst screen or bottom 23 is provided extending over the entire free cross sectional area of the heat exchanger inside of tube portions 15 and supporting the catalyst mass 26 with which the space between tubes 22 is filled from bottom 23 up to about the level of the joint between flanges 2 and 5.

The crude gas supply inlet 24 is provided in reactor bottom 6 which is lined with insulating layer portion 10, while the outlet 25 for the gaseous methanol is provided in cover 4. The crude gas flows through the catalyst bed 26 between tubes 22 and their bent end portion 20, 21 and, after being brought to reaction with the aid of the catalyst, flows out through outlet 25 as methanol gas.

The closed circumferential wall of exchanger tubes 12 snugly applies against insulating layer 8 of the reactor. Upon loosening cover 4 and the insulating layer portion 9 supported thereon, the entire heat exchanger 11, with its outer wall 13 and the catalyst bed, can be lifted upwardly and removed from the reactor. Then, after loosening screen or bottom 23 partly or completely, the catalyst can be taken out and the structure can be filled with a new catalyst charge. The exchanger tubes can easily be dismounted, or secured in place, from above or from below, while the entire structure is removed from the reactor housing.

In the embodiment of FIG. 2, again a pressure jacket 51 is provided which is lined with an insulating layer 52. Jacket 51 is provided with a flange 53 to be connected to the flange 54 of the cover 55. Crude gas is supplied through a connection 56 about at half the height of the reactor, extending through jacket 51 and insulating layer 52. Like in the embodiment of FIG. 1, insulating layer 52 embraces a heat exchanger. The exchanger comprises an outer wall 57 of finned tubes 58, with an entrance left permitting the crude gas to flow to the interior, and a nest of exchange tubes 61 opening by their bent end portions 59-60 into wider tube portions 62,63 of finned tubes 58, which wider tube portions in turn open into ring conduits 62a, 63a, respectively, for circulating the coolant.

One catalyst supporting screen 64 is provided at a level slightly above supply connection 56, and another catalyst supporting screen 64a is provided slightly above the level of ring conduit 63a. In this embodiment, the bottom 65 of the reactor as well as the insulating layer portion 66 applying thereto are integral with pressure jacket 51 and insulating layer 52 of the reactor. This insulated bottom 65,66 and insulated cover 55,68 are provided with outlets 67,69 respectively, for removing the methanol gas.

In either of the embodiments of FIGS. 1, 2, exchanger tubes 22, 61 are provided with fins 70,71 which extend in pairs opposite to each other. The fins project so as to form closed passageways 72 to be filled with the catalyst mass and through which the gas flows. The gas is thus to a large extent prevented from straying into neighboring passageways, and thus from skirting tubes 22,61 irregularly. This also makes it possible to remove the catalyst for exchange successively, by opening the catalyst supporting screen step by step, and thus to facilitate the operation.

The provision of two superimposed catalyst beds in a reactor is known in itself from German OS No. 30 228.15. The features connected thereto are therefore claimed only in connection with the other features of the invention.

It will be understood that an approximately cylindrical jacket 15,57 may be provided as an equivalent as well.

Figure 4:
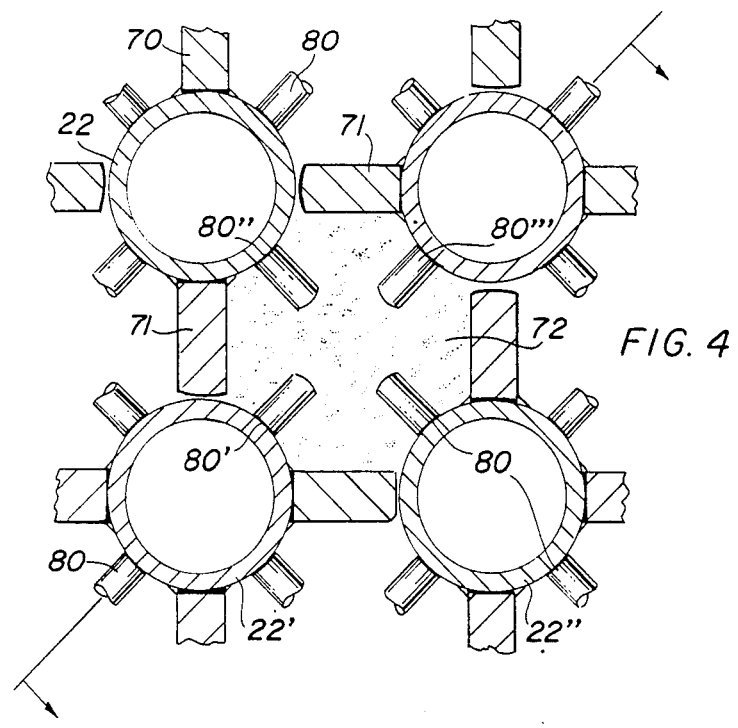
FIG. 4 is another horizontal sectional view similar to FIG. 3.
Figure 5:
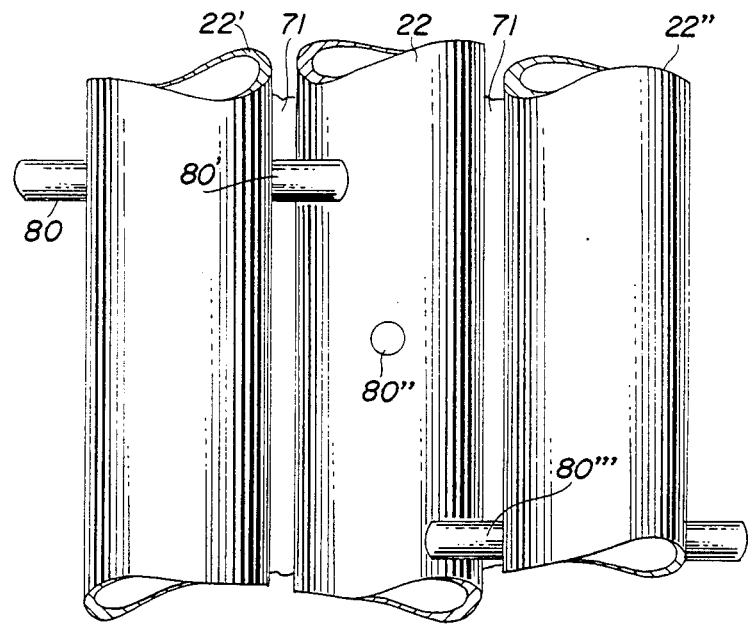
FIG. 5 is a sectional view taken along the line V—V of FIG. 4.

According to FIGS. 4 and 5, tubes 22 are provided with radially outwardly extending pins 80 which are uniformly distributed over the circumference and project into the flow passageways, thus into the catalyst bed. As shown in FIG. 4, the pins project from the tubes star-like. However, they are provided by pairs at different levels; for example, pin 80' in FIG. 5 extends at a higher level than pin 80" which again extends at a higher level than pin 80'".

The pins project to a distance of about $\frac{1}{4}$ to $\frac{1}{3}$ of the mutual spacing of diagonally adjacent tubes, for example tubes 22 and 22" of FIG. 4.

Preferably, the pins are shot into the tube walls.

The pins might have a rectangular cross section or be shaped as rivets.

While specific embodiments of the invention have been shown and described in detail to illustrate the application of the principles of the invention, it will be understood that the invention may be embodied otherwise without departing from such principles.

What is claimed is:

1. A reactor comprising, a vertically elongated cylindrical housing, a heat exchanger within said housing, including an outer heat exchanger wall of finned tubes and an interior array of vertically extending heat exchanger tubes each having upper and lower horizontally extending end portions, said finned tubes of said outer heat exchanger wall having top and bottom header portions into which said upper and lower horizontally extending portions of said heat exchanger tubes extend respectively, an upper header ring connected to said top header portions, a lower header ring connected to said bottom header portions, a gas permeable floor in a lower portion of said housing connected to said heat exchanger wall above said lower header ring and below said lower horizontally extending end portions, a catalyst bed supported on said floor and filling the spaces between said heat exchanger tubes and said finned tubes of said outer heat exchanger above said floor, said housing having a removable cover of a diameter larger than said outer heat exchanger wall and said floor permitting said heat exchanger wall with said floor, said heat exchanger tubes and said catalyst bed to be lifted out of said housing, each of said heat exchanger tubes having a plurality of radially extending fins, each heat exchanger tube mounted in said housing such that each fin engages an adjacent heat exchanger tube in a manner such that said heat exchanger tubes and fins togehter form closed vertical passages in said housing for said catalyst, each heat exchanger tube having a plurality of radially extending pins which extend into said passages and extend symmetrically outwardly form said heat exchanger tubes to project from said heat exchanger tubes at different levels.

2. A reactor according to claim 1, including means for supplying a coolant to one of said header rings for flow through said tubes to the other of said header rings, means for supplying gas for flow through said catalyst bed in a one direction and for exit at the opposite end of said housing.

3. A reactor according to claim 1, wherein said housing has a removable cover adjacent both the top and bottom ends, including a gas connection to said reactor at the both the top and bottom covers.

4. A reactor according to claim 1, wherein said catalyst mass fills the space above said bottom in said housing up to the joint of said cover with said housing.

5. A reactor according to claim 1, wherein said pins are shot into the tube walls.

6. A reactor according to claim 1 wherein said fins are welded to said tubes in pairs.

* * * * *